United States Patent [19]

Bremer

[11] Patent Number: 4,612,930
[45] Date of Patent: Sep. 23, 1986

[54] HEAD FIXATION APPARATUS INCLUDING CROWN AND SKULL PIN

[76] Inventor: Paul W. Bremer, 433 Margaret St., Jacksonville, Fla. 32204

[21] Appl. No.: 713,552

[22] Filed: Mar. 19, 1985

[51] Int. Cl.⁴ .............................................. A61B 17/00
[52] U.S. Cl. ................................ 128/303 B; 269/328; 411/386
[58] Field of Search ........................... 128/303 B, 305; 269/328; 411/386

[56]  References Cited

U.S. PATENT DOCUMENTS

| | | | |
|---|---|---|---|
| 1,398,842 | 11/1921 | Cruse | 128/303 B |
| 3,336,922 | 8/1967 | Taylor | 128/75 |
| 4,055,862 | 11/1977 | Farling | 3/1.91 |
| 4,146,793 | 3/1979 | Bergstrom et al. | 250/444 |
| 4,256,112 | 3/1981 | Kopf et al. | 128/303 B |
| 4,465,069 | 8/1984 | Barbier et al. | 128/303 B |
| 4,475,550 | 10/1984 | Bremer et al. | 128/303 B |

OTHER PUBLICATIONS

Brochures of Kyocera International, Inc., "Kyocera and Bioceram" and "Custom Ceramic Implants", 1983.
Thompson "The 'Halo' Traction Apparatus", Journal of Bone and Joint Surgery, Aug., 1962, vol. 44B, No. 3, pp. 665–661.
Nickel et al "The Halo", The Journal of Bone and Joint Surgery, vol. 50A, No. 7, Oct., 1968, pp. 1400–1409.

Primary Examiner—Stephen F. Husar
Attorney, Agent, or Firm—Nixon & Vanderhye

[57] ABSTRACT

The skull of a patient is immobilized utilizing a generally ring-shaped member (crown) that can be used in place of a conventional halo or tongs, and is affixed to the patient's skull utilizing particularly advantageous skull pins. The crown has a first major portion which is in a first plane, and has a second portion extending at an angle out of the first plane. Preferably it has a generally horseshoe shape in plan view, with first and second ends spaced from each other, those ends being part of the second portion of the crown. Skull pins pass through threaded openings in the crown, including threaded openings in the second portion to attach the crown below a capital distal plane extending between the top of the ears and the top of the eyes of the patient's head. The rigid crown is preferably of a boron fiber or graphite fiber reinforced plastic. The skull pins, which do not artifact any more than bone does, comprise an exteriorly threaded cylinder of plastic (e.g. boron or carbon fiber reinforced plastic), and a skull engaging portion rigidly connected to the cylinder and extending outwardly from a first end of the cylinder and terminating in a pointed tip. The skull engaging portion is of a ceramic material, preferably a single crystal alumina ceramic material.

20 Claims, 4 Drawing Figures

U.S. Patent  Sep. 23, 1986  4,612,930
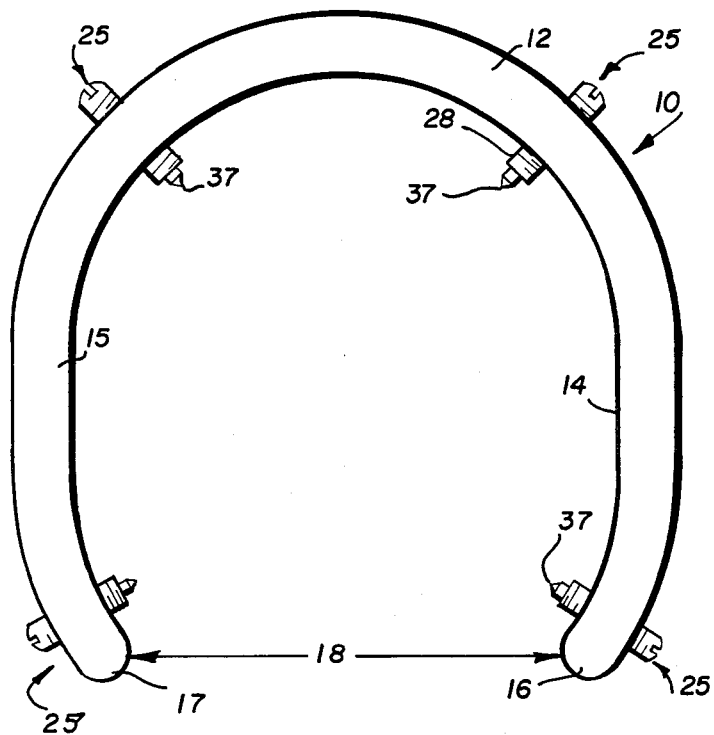
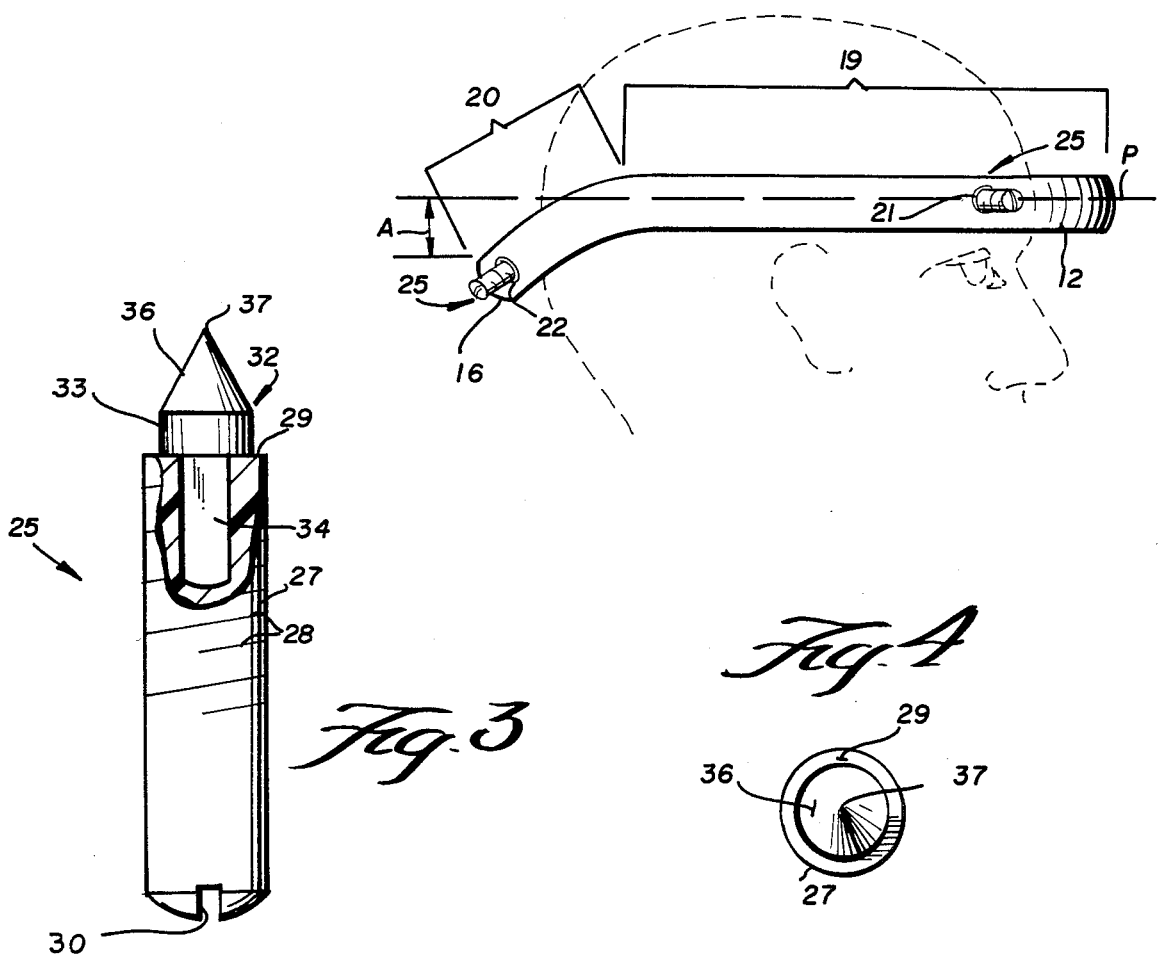

HEAD FIXATION APPARATUS INCLUDING CROWN AND SKULL PIN

BACKGROUND AND SUMMARY OF THE INVENTION

In many medical treatment and operative procedures it is necessary to hold a patient's head in a particular position. For instance a patient's head is held in a fixed predetermined position while a fracture or dislocation of the cervical spine is healing, as by utilizing a conventional halo traction device, or during neurosurgery, utilizing an operating table head holder. While the patient's head is being immobilized, however, it may also be desirable to subject the patient's skull to an imaging procedure, such as a CT scan, digital subtraction angiography, sonography, magnetic resonance imaging, computer enhanced flat film X-raying, and the like. Therefore it is highly desirable that the affixation apparatus be made of a material which does not artifact significantly (e.g. any more than bone does).

According to a first aspect of the present invention, a skull pin is provided which does not artifact any more than bone does. The skull pin may be used with a conventional halo, with an operating table head holder, or with other skull fixation apparatus used in medical treatment or operative procedures. Typically skull pins are made out of stainless steel and are a total block to CT or magnetic resonance imaging of the skull. This greatly limits the physician in the types of apparatus that may be utilized for head immobilization for a number of medical operative procedures. For instance accident victims may have brain swelling caused by impact, which can result in inter-cranial pressure and resulting death or brain damage. Imaging of the brain, as with a CT scanner, is a desirable way to check for brain swelling. If the accident victim has a broken neck, or the like, the physician will not utilize a halo or tongs to stabilize the broken neck (even though they are highly desirable for that purpose) because the physician cannot then monitor brain swelling utilizing imaging because of the blockade resulting from stainless steel skull pins, or the material of the halo or tongs itself.

According to the present invention, a skull pin is provided which allows effective imaging of a patient's skull, yet provides the desired skull fixation in an effective manner. The skull pin according to the invention includes a skull engaging portion which terminates in a pointed tip, and is of ceramic. Most desirably the skull engaging portion is of a single crystal ceramic material, such as single crystal alumina ceramic commercially sold under the trademark "BIOCERAM" by Kyocera International, Inc. of West Los Angeles, Calif. This material does not artifact any more than does bone; however it has a brittleness that does not allow the skull pin to be made wholly of it. Therefore the skull pin according to the invention also comprises an exteriorly threaded elongated cylinder of plastic, having first and second ends. Preferably the plastic is a carbon fiber reinforced plastic, or boron fiber reinforced plastic, such as shown in U.S. Pat. Nos. 4,055,862 and 4,146,793. The skull engaging portion is fixed to the plastic cylinder, as by an integral shaft of the skull engaging portion extending into an opening within the cylinder and adhering to the cylinder along the entire area thereof. The cylinder also has a screwdriver blade-receiving slot, or other structure to allow driving of the skull pin, at the second end thereof.

According to the present invention, there also is provided a generally ring-shaped member for skull immobilization that not only does not interfere with imaging but also provides fixation in a very secure manner. This generally ring-shaped member, which may be referred to as a "crown", can take the place of halos for most procedures in which halos are now utilized. It is rigid and has a plurality of threaded openings therein for receipt of skull pins. It preferably is of carbon fiber or boron fiber reinforced plastic, and has a shape and dimensions so as to maintain rigidity during use. A first, major portion thereof is in a first plane, and a second portion thereof slants out of the first plane. During use in a medical treatment or operative procedure, the second, out of plane portion extends downwardly to a position below the "equator" of the patient's head, that is to a position below a capital-distal plane extending between the top of the patient's ears and the top of his eyes. The crown is affixed to the patient's head by skull pins passing through openings in the second portion of the crown. Preferably the crown also has a generally horseshoe shape in plan view, with first and second ends spaced from each other, the first and second ends comprising part of the second portion of the crown. Such a shape facilitates utilization of the crown.

It is the primary object of the present invention to provide for affixation of a patient's head, in an effective manner, during a medical treatment or operative procedure in such a way so that imaging of the patient may be practiced without unacceptable blocking. This and other objects of the invention will become clear from an inspection of the detailed description of the invention, and from the appended claims.

BRIEF DESCRIPTION OF THE DRAWINGS

FIG. 1 is a top plan view of an exemplary crown according to the present invention;

FIG. 2 is a side view of the crown of FIG. 1, showing it in an operative position on a patient's head;

FIG. 3 is a side view, partly in cross-section and partly in elevation, of an exemplary skull pin according to the present invention; and FIG. 4 is an end view, looking in at the point, of the skull pin of FIG. 3.

DETAILED DESCRIPTION OF THE DRAWINGS

An exemplary apparatus according to the present invention for holding a living patient's head in a predetermined desired position during a medical treatment or operative procedure is shown generally by reference 10 in FIG. 1. The apparatus comprises a generally ring-shaped member 12 which is rigid and preferably is constructed of a material that does not artifact substantially, so that it does not cause blockade during CT scanning, magnetic resonance imaging, or the like. Preferably the generally ring-shaped member 12 (denoted a "crown") is quadrate in cross-section (e.g. a square ¾ inch on a side, or a rectangle ¾ inch by ½ inch), and is made of carbon fiber reinforced plastic material, or boron fiber reinforced plastic material. A wide variety of such materials may be utilized, as long as they have the desired qualities of strength and rigidity to perform the skull immobilization function. Exemplary materials are shown in U.S. Pat. Nos. 4,055,862 and 4,146,793.

While the crown 12 may be circular or oval in plan view, in order to faciliate utilization thereof for a number of procedures, preferably it has a generally horseshoe shape in plan view, as can be seen FIG. 1. That is, it has side portions 14, 15 thereof which terminate in ends 16, 17. The ends are spaced from each other a distance 18 (see FIG. 1), that preferably is greater than the width of a patient's head.

The crown 12 according to the present invention includes a first, major, portion 19 thereof (see FIG. 2) which is disposed in a first plane, which includes the majority of the side portions 14, 15 thereof. The crown 12 also includes, however, adjacent the ends 16, 17 thereof, a second portion 20 which slants at an angle with respect to the first portion 19 (see FIG. 2) so that there is a significant vertical spacing A (see FIG. 2) between a center line of the first portion 19, and the ends 16, 17 (e.g. as by bending the end portions about a three inch radius). Any desired amount and extent of slant may be provided for the second portion 20 so as to accomplish a desirable result of providing a portion of the crown 12 below the "equator" of the patient's head during use. Such a position of the portion 20 is illustrated with respect to a patient's head in FIG. 2. Three or four standard sizes of crowns can accommodate most of the population.

Note that the plane of the first portion 19 in use of the crown 12 extends in a plane P which is generally from a top portion of the patient's eyes to the tops of his ears, but so that it does not touch the ears. This may be referred to as a capital-distal plane. The portion 20, particularly end 16 thereof, extends below this plane so that it actually is below the "equator" of the head. When it is affixed in this position there is less tendency for the crown 12 to slip than, for example, there would be a tendency for a conventional halo to slip when affixed to a patient's skull.

The apparatus 10 also includes means defining a plurality of screw-threaded openings, such the openings illustrated generally by reference numerals 21, 22 in FIG. 2, extending through the crown 12 toward the interior thereof. These openings 21, 22 are adapted to receive exteriorly threaded skull pins 25. Note that it is preferred that at least one of the openings (and preferably two openings) be provided in the second portion 20 of the crown 12 so that a pin 25 extending therethrough will penetrate the patient's head below the capital-distal plane P, so that the crown 12 will hold the patient's head more securely, with less chance of slippage. In particular see the position of the leftmost pin 25, in association with the opening 22, adjacent the end 16 of crown 12, in FIG. 2, with a like pin 25 being provided adjacent the end 17.

In use, the crown 12 may be employed for any conventional type of medical treatment or operative procedure where a halo or tongs might be utilized. For instance it may be connected up to traction apparatus to hold a patient's head in a fixed predetermined position while a fracture or dislocation of the cervical spine is healing. The particular apparatus for connecting the crown 12 up to traction apparatus, or like stabilizing structures, is not illustrated in FIGS. 1 and 2, but may take a wide variety of forms. For example see U.S. Pat. Nos. 4,475,550 and 3,336,922, which illustrate merely two exemplary known arrangements.

The skull pins 25 according to the present invention (see FIGS. 3 and 4) are particularly designed so that they do not artifact significantly (e.g. any more than bone does) and thus may be readily employed even when the patient must be subjected to imaging techniques. While conventional stainless steel skull pins could be utilized with the crown 12, the skull pin 25 according to the present invention are preferred.

As seen in FIG. 3, an exemplary skull pin 25 according to the present invention comprises an elongated cylinder 27 having external threads 28 formed thereon, which threads will cooperate with the internal threadings of the openings 21, 22 in crown 12. The cylinder has a first end 29, and a second end in which a screwdriver blade-receiving slot 30, or like structure, is formed. The cylinder 27 is made of plastic, such as a carbon fiber or boron fiber reinforced plastic, that has sufficient rigidity and strength to be utilized as a skull pin, but is not brittle and does not artifact.

The skull pin 25 also includes a skull engaging portion 32 thereof. The skull engaging portion 32 extends outwardly from the first end 29 of the cylinder 27, and terminates in a pointed tip 37. The portion 32 is of a ceramic material. Preferably it is of single crystal ceramic material, such as single crystal alumina ceramic, such as "BIOCERAM". Such a material is ideally suited for skull penetration, yet does not artifact any more than bone does.

The portion 32 is rigidly connected to the cylinder 27 by any suitable mechanism. In the preferred embodiment illustrated in FIG. 3, the portion 32 includes a body portion 33, a shaft 34, and a conical portion 36 (terminating in tip 37) which extends outwardly on the opposite side of the body 33 from the shaft 34. The shaft 34 is inserted in a mold for the construction of the cylinder 27, and suitable plastic (such as carbon fiber reinforced plastic) is injected into the mold and solidifies around the shaft 34 during formation of the cylinder 27, so that the shaft 34 is held tightly to the cylinder 27. Alternatively, the cylinder 27 could be injection molded of plastic with a bore in the end 29 thereof having basically the same cross-sectional shape and dimensions as the shaft 34, and the shaft 34 could then be held in place in the bore by an interference fit, by an epoxy adhesive, or by another adhesive or mechanical system.

If desired, the second end 30 of the cylinder 27 may be constructed so that it has a torque limiting function. That is it can be constructed so that if there is an attempt to apply torque greater than a certain amount to the cylinder 27 during the threading thereof into the patient's skull, failure of the material will occur so that further tightening is not possible.

While the skull pin 25 according to the invention is particularly suited for use with a crown 12, it is also utilizable with any conventional structure wherein attachment of another component to a patient's skull is desired. For instance it may be utilized with conventional halos, and conventional (or to be developed) operating table head holders commonly utilized by neurosurgeons.

The apparatus 10 according to the invention has a wide variety of uses for medical treatment and operative procedures. One exemplary (only) use thereof is as follows:

The crown 12 is slipped into operative association with the patient's head, surrounding his skull, by moving the crown 12 with respect to the patient's skull so that the ends 16, 17 pass on either side of the patient's skull. The crown 12 is then disposed so that the second portion 20 thereof is below the capital-distal plane P, and then all the skull pins 25 (i.e. all four skull pins in the embodiment of the invention illustrated in FIG. 1) are threaded through the crown 12 so that they are in operative association with the patient's skull. The skull pins associated with the openings 22, adjacent the ends 16, 17 of the crown 12, operatively engage the patient's head below the "equator" and minimize the possibility that the crown 12 will slip.

After attachment of the crown 12 to the patient's head in the position illustrated in FIG. 2, the crown 12 is stabilized, as by attaching it to stationary traction components. Should it then be necessary to imagine the patient's skull, however, for any reason (such as to check for brain swelling), the patient is merely moved into operative association with a CT scanner, magnetic resonance imaging device, or other imaging system, and imaging is practiced in a conventional manner. The skull pins 25 in the crown 12 do not significantly block the imaging, so that a proper image can be obtained.

It will thus be seen that according to the present invention a simple yet effective apparatus and procedure for facilitating holding of a living patient's head in a predetermined position during a medical treatment or operative procedure has been provided. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and procedures.

What is claimed is:

1. A skull pin comprising:
an exteriorly threaded elongated cylinder of plastic, having first and second ends; and
a skull-engaging portion connected to said cylinder and extending outwardly from said first end thereof, and terminating in a pointed tip, said skull engaging portion of a material which does not artifact significantly more than bone does.

2. A skull pin as recited in claim 1 wherein said skull engaging portion is of single crystal alumina ceramic material.

3. A skull pin as recited in claim 2 further comprising means defining a slot at said second end of said cylinder for receipt of a screwdriver blade.

4. A skull pin as recited in claim 2 wherein said skull engaging portion includes: a conical portion terminating in said pointed tip; a body portion; and a shaft; said shaft received within an opening in said cylinder and rigidly connected to said cylinder.

5. A skull pin as recited in claim 1 wherein said skull engaging portion includes: a conical portion terminating in said pointed tip; a body portion; and a shaft; said shaft received within an opening in said cylinder and rigidly connected to said cylinder; said body, conical portion, and shaft comprising an integral piece of ceramic.

6. A skull pin as recited in claim 1 wherein said plastic is selected from the group consisting essentially of boron fiber reinforced plastics and carbon fiber reinforced plastics.

7. Apparatus for use with a living patient to facilitate immobilization of the patient's skull during a medical treatment or operative procedure, comprising:
a generally ring-shaped rigid member having interior cross-dimensions larger than the diameter of the patient's head;
means defining a plurality of threaded openings extending through said generally ring-shaped rigid member;
a plurality of skull pins received in said openings and threadably adjustable in said openings to adjust the extent of penetration of each of said skull pins into an interior volume defined by said generally ring-shaped rigid member; and
each skull pin comprising: an exteriorly threaded elongated cylinder of plastic, having first and second ends; and a skull engaging portion rigidly connected to said cylinder and extending outwardly from said first end thereof and terminating in a pointed tip, said skull engaging portion of ceramic material.

8. Apparatus as recited in claim 7 wherein said skull engaging portion is of single crystal alumina ceramic material.

9. Apparatus as recited in claim 8 wherein said skull engaging portion includes: a conical portion terminating in said pointed tip; a body portion; and a shaft; said shaft received within an opening in said cylinder and rigidly connected to said cylinder.

10. Apparatus as recited in claim 8 wherein said plastic is selected from the group consisting essentially of boron fiber reinforced plastics and carbon fiber reinforced plastics.

11. Apparatus for use with a living patient to facilitate immobilization of the patient's skull during a medical treatment or operative procedure, comprising:
a generally ring-shaped rigid member having interior cross-dimensions larger than the diameter of the patient's head;
means defining a plurality of threaded openings extending through said generally ring-shaped rigid member;
a plurality of skull pins received in said openings and threadably adjustable in said openings to adjust the extent of penetration of each of said skull pins into an interior volume defined by said generally ring-shaped rigid member; and
said ring member having a first, major, portion thereof disposed in a first plane, and having a second portion thereof slanting at an angle out of said first plane; at least one of said openings receiving a skull pin being disposed in said second portion, out of said first plane.

12. Apparatus as recited in claim 11 wherein said generally ring-shaped rigid member has a generally horseshoe configuration in plan view, including first and second ends, said first and second ends being spaced from each other and part of said second portion slanting out of said first plane.

13. Apparatus as recited in claim 12 wherein said generally ring-shaped rigid member is an integral piece of material selected from the group consisting essentially of boron fiber reinforced plastic materials and carbon fiber reinforced plastic materials.

14. Apparatus as recited in claim 11 wherein each of said skull pins comprises an elongated exteriorly threaded cylinder of plastic material, having first and second ends; and a skull engaging portion rigidly connected to said cylinder and extending outwardly from said first end thereof and terminating in a pointed tip, said skull engaging portion of single crystal ceramic material.

15. Apparatus as recited in claim 11 wherein said generally ring-shaped rigid member is an integral piece of material selected from the group consisting essentially of boron fiber reinforced plastic materials and carbon fiber reinforced plastic materials.

16. Apparatus as recited in claim 15 wherein each of said skull pins comprises an elongated exteriorly threaded cylinder of plastic material, having first and second ends; and a skull engaging portion rigidly connected to said cylinder and extending outwardly from said first end thereof and terminating in a pointed tip, said skull engaging portion of ceramic material.

17. A method of holding a living patient's head in a predetermined desired position during a medical treatment or operative procedure, utilizing a generally ring-shaped rigid member having interior cross-dimensions larger than the diameter of the patient's head, means defining a plurality of threaded openings through the ring-shaped member adapted to receive skull pins therein, and having a first major portion thereof disposed in a first plane and a second portion slanting out of the first plane; said method comprising the steps of:
(a) slipping the ring-shaped member into operative association with the patient's head surrounding the patient's head;
(b) disposing the ring-shaped member so that the second portion thereof is below a capital-distal plane extending between the top of the ears and eyes of the patient;
(c) attaching the ring-shaped member at the position recited in step (b) with skull pins passing through the threaded openings in the ring-shaped member, so that the ring-shaped member is above the ears but so that the second portion thereof is below said plane; and
(d) stabilizing the ring-shaped member as a medical treatment or during practice of a medical operative procedure.

18. A method as recited in claim 17 wherein the generally ring-shaped member has a generally horseshoe shape in plan view, with first and second ends spaced from each other, the first and second ends spaced from each other a dimension greater than the width of the patient's head and the first and second ends comprising part of the second portion of the ring-shaped member; and wherein step (a) is practiced by moving the generally ring-shaped member with respect to the patient's head so that the patient's head passes between the first and second ends.

19. A method as recited in claim 17 wherein step (c) is practiced by passing skull pins through openings formed in the second portion of the generally ring-shaped member so that the skull pins engage the patient's head below said plane.

20. A method as recited in claim 17 wherein the generally ring-shaped member and skull pins are made of materials which will not significantly artifact during imaging of the patient's skull, and comprising the further step of, after step (d), imaging the patient's skull.

* * * * *